United States Patent
Maekita

(10) Patent No.: US 8,920,060 B2
(45) Date of Patent: Dec. 30, 2014

(54) ROTATION RESTRICTING DEVICE, ROBOT JOINT AND WALKING ASSISTANCE DEVICE

(75) Inventor: Wataru Maekita, Miyoshi (JP)

(73) Assignee: Toyota Jidosha Kabushiki Kaisha, Toyota-Shi (JP)

(*) Notice: Subject to any disclaimer, the term of this patent is extended or adjusted under 35 U.S.C. 154(b) by 839 days.

(21) Appl. No.: 13/140,633
(22) PCT Filed: Apr. 16, 2010
(86) PCT No.: PCT/JP2010/056842
§ 371 (c)(1), (2), (4) Date: Jun. 17, 2011
(87) PCT Pub. No.: WO2011/129013
PCT Pub. Date: Oct. 20, 2011

(65) Prior Publication Data
US 2012/0041348 A1 Feb. 16, 2012

(51) Int. Cl.
| F16C 11/10 | (2006.01) |
| F16C 11/00 | (2006.01) |
| F16P 3/00 | (2006.01) |
| A61H 1/00 | (2006.01) |
| B25J 9/00 | (2006.01) |
| G05G 5/04 | (2006.01) |
| B25J 9/10 | (2006.01) |
| A61F 5/01 | (2006.01) |
| A61F 2/68 | (2006.01) |

(52) U.S. Cl.
CPC ............... *B25J 9/101* (2013.01); *B25J 9/0006* (2013.01); *A61F 2005/0158* (2013.01); *A61F 2005/0167* (2013.01); *G05G 5/04* (2013.01); *A61F 2002/6863* (2013.01); *A61F 5/0125* (2013.01); *A61F 2002/6854* (2013.01); *A61F 5/0102* (2013.01)
USPC ............... 403/117; 403/113; 601/33; 601/34; 192/139; 192/142 R; 74/526; 74/527

(58) Field of Classification Search
CPC .......... B25J 9/101; B25J 9/0006; G05G 5/04; A61F 5/0102; A61F 2005/0167; A61F 2005/0158; A61F 2002/6854; A61F 2002/6863

USPC ................. 601/5, 23, 33–35; 602/23, 24, 26; 403/DIG. 1, 112, 113, 117; 74/526, 74/527; 192/139, 142 R, 143, 138; 70/275, 70/276, 277, 278.1, 278.7
See application file for complete search history.

(56) References Cited

U.S. PATENT DOCUMENTS

| 4,828,094 A * | 5/1989 | Torii et al. ............ 192/139 |
| 4,934,504 A | 6/1990 | Torii et al. |

(Continued)

FOREIGN PATENT DOCUMENTS

| JP | 58-59786 A | 4/1983 |
| JP | 60-134590 U | 9/1985 |
| JP | 61-144991 U | 9/1986 |
| JP | 61-297088 A | 12/1986 |

(Continued)

OTHER PUBLICATIONS

Translation of International Search Report mailed Jul. 13, 2010 of PCT/JP2010/056842.

*Primary Examiner* — Justine Yu
*Assistant Examiner* — Douglas Sul
(74) *Attorney, Agent, or Firm* — Kenyon & Kenyon LLP

(57) ABSTRACT

A rotation restricting device for restricting the rotation of a rotating part with respect to a base part, comprising a stopper supported so as to be capable of rotating around an axis of rotation of the base part, a lock mechanism capable of switching between a state preventing and a state allowing the rotation of the stopper with respect to the base part, a first block provided on the rotating part and capable of moving between a position interfering with and a position not interfering with a rotation path of the stopper, and a second block provided on the rotating part and capable of moving between a position interfering with and a position not interfering with the rotation path of the stopper. In a state where the rotation of the rotating part with respect to the base part is not restricted, both the first block and the second block are in the position interfering with the rotation path of the stopper, and the stopper is positioned between the first block and the second block.

4 Claims, 9 Drawing Sheets

(56) References Cited

U.S. PATENT DOCUMENTS

| | | | |
|---|---|---|---|
| 5,771,753 A * | 6/1998 | Kwon et al. | 74/526 |
| 5,938,629 A * | 8/1999 | Bloedau | 602/16 |
| 6,966,882 B2 * | 11/2005 | Horst | 601/5 |
| 7,037,287 B2 * | 5/2006 | Cormier et al. | 602/23 |
| 7,083,583 B2 * | 8/2006 | Opahle et al. | 602/16 |
| 2013/0006388 A1 * | 1/2013 | Pusch et al. | 623/43 |

FOREIGN PATENT DOCUMENTS

| | | |
|---|---|---|
| JP | 63-102891 A | 5/1988 |
| JP | 02-015991 A | 1/1990 |
| JP | 2-122792 U | 10/1990 |
| JP | 05-023994 A | 2/1993 |
| JP | 05-228887 A | 9/1993 |
| JP | 09-085670 A | 3/1997 |
| JP | 2004-188530 A | 7/2004 |

\* cited by examiner

ROTATION RESTRICTING DEVICE, ROBOT JOINT AND WALKING ASSISTANCE DEVICE

This is a 371 national phase application of PCT/JP2010/056842 filed 16 Apr. 2010, the content of which is incorporated herein by reference.

TECHNICAL FIELD

The present invention relates to a rotation restricting device, a robot joint comprising the rotation restricting device, and a walking assistance device comprising the robot joint.

BACKGROUND ART

In recent years, a walking assistance device has been developed that is fitted from an upper leg to a foot (a part beyond the ankle joint) of a user, and assists the movement of a knee joint of the user by applying torque. This type of walking assistance device comprises a foot frame, lower leg frame, upper leg frame, and actuator. The foot frame is configured such that it can be fitted onto the user's foot. The lower leg frame is connected, by a first rotary joint, such that it can rotate with respect to the foot frame. The upper leg frame is configured such that it can be fitted onto the user's upper leg. Further, the upper leg frame is connected, by a second rotary joint, such that it can rotate with respect to the lower leg frame. The actuator is capable of applying torque to the second rotary joint. In this walking assistance device, the first rotary joint rotates coaxially with the user's ankle joint, and the second rotary joint rotates coaxially with the user's knee joint. The movement of the user's knee joint is assisted by torque applied to the second rotary joint by the actuator. The operation of the actuator is controlled by a control unit.

To ensure the safety of the user in the case of the walking assistance device malfunctioning, a configuration is desired that can restrict the rotation of the second rotary joint which is driven by the actuator. E.g., a configuration is desired that, by restricting the rotation of the second rotary joint, can ensure the safety of the user in a state where the user is fitted with the walking assistance device, even if the control unit or the actuator has malfunctioned. In the present specification, "restricting the rotation" means restricting the range of rotation.

A technique of Japanese Published Utility Model Application No. H02-122792 is known as a technique for restricting the rotation of a robot joint such as the second rotary joint of the walking assistance device. A stopper mechanism is taught in Japanese Published Utility Model Application No. 1102-122792, this stopper mechanism having one rotation side fitting, one fixed stopper and two retractable stoppers. During normal operation of the robot joint, the retractable stoppers are in a retreated position and do not interfere with the rotation side fitting. Consequently, the robot joint can rotate until the rotation side fitting and the fixed stopper make contact, and the rotation range of the robot joint is regulated by the fixed stopper. In the case of wanting to restrict the rotation range of the robot joint more narrowly than the rotation range during normal operation, the retractable stoppers are made to protrude to a position where they interfere with the rotation side fitting. In this state, the robot joint can rotate until the rotation side fitting and the retractable stoppers make contact. Consequently, the rotation range of the robot joint can be restricted more narrowly than the rotation range during normal operation.

SUMMARY OF INVENTION

Technical Problem

In the technique of Japanese Published Utility Model Application No. H02-122792, the rotation of the robot joint is restricted by causing the retractable stoppers to interfere with the rotation side fitting. Consequently, the restricted rotation range of the robot joint is regulated by the position of the retractable stoppers. To change this restricted rotation range, the setting position of the retractable stoppers, or the setting position of the fixed stopper must be re-adjusted, requiring the effort of an operation to replace the part. A technique is desired whereby the rotation range of a robot joint can be adjusted more conveniently.

The present invention solves the above problem. The present invention teaches a technique whereby the rotation range of the robot joint can be adjusted conveniently.

Solution to Technical Problem

The present invention is realized as a rotation restricting device for restricting the rotation of a rotating part with respect to a base part. This rotation restricting device comprises a stopper supported so as to be capable of rotating around an axis of rotation of the base part, a lock mechanism capable of switching between a state preventing and a state allowing the rotation of the stopper with respect to the base part, a first block provided on the rotating part and capable of moving between a position interfering with and a position not interfering with a rotation path of the stopper, and a second block provided on the rotating part and capable of moving between a position interfering with and a position not interfering with the rotation path of the stopper. In this rotation restricting device, in a state where the rotation of the rotating part with respect to the base part is not restricted, both the first block and the second block are in the position interfering with the rotation path of the stopper, and the stopper is positioned between the first block and the second block.

In the above rotation restricting device, while the lock mechanism is allowing the rotation of the stopper, the stopper can rotate around the axis of rotation of the base part. Since the stopper is positioned between the first block and the second block in the state where the rotation of the rotating part with respect to the base part is not restricted, the stopper makes contact with the first block or the second block when the rotating part rotates with respect to the base part and, following the rotation of the rotating part with respect to the base part, the stopper also rotates with respect to the base part. When the lock mechanism prevents the rotation of the stopper, the position of the stopper with respect to the base part is fixed, and the rotation of the rotating part with respect to the base part is restricted by the stopper making contact with the first block or second block. The restricted rotation range in this rotation restricting device is regulated by the position in which the stopper is fixed. Since the stopper follows the rotation of the rotating part and rotates with respect to the base part while the lock mechanism is allowing the rotation of the stopper, as described above, the stopper can be fixed in a desired position by switching the lock mechanism appropriately. According to this rotation restricting device, the rotation range of the rotating part with respect to the base part can be adjusted conveniently.

In the aforementioned rotation restricting device, it is preferred that a space between the first block in the position interfering with the rotation path of the stopper and the second block in the position interfering with the rotation path of the stopper is equal to a width of the stopper along its rotation direction.

According to the aforementioned rotation restricting device, by moving the first block and the second block to the position interfering with the rotation path of the stopper, the stopper can be gripped without a clearance therebetween by the first block and second block. While the stopper is rotating with respect to the base part following the rotation of the rotating part, the relative positional relationship of the stopper and the rotating part can be maintained, and the position in which the stopper is fixed by the lock mechanism can be set accurately. The restricted rotation range can be set accurately.

Moreover, the present invention can also be realized as a robot joint comprising the aforementioned rotation restricting device, and can also be realized as a walking assistance device comprising that robot joint.

Advantageous Effects of Invention

According to the present invention, the rotation range of the robot joint can be adjusted conveniently.

DESCRIPTION OF EMBODIMENTS

Figure 1:
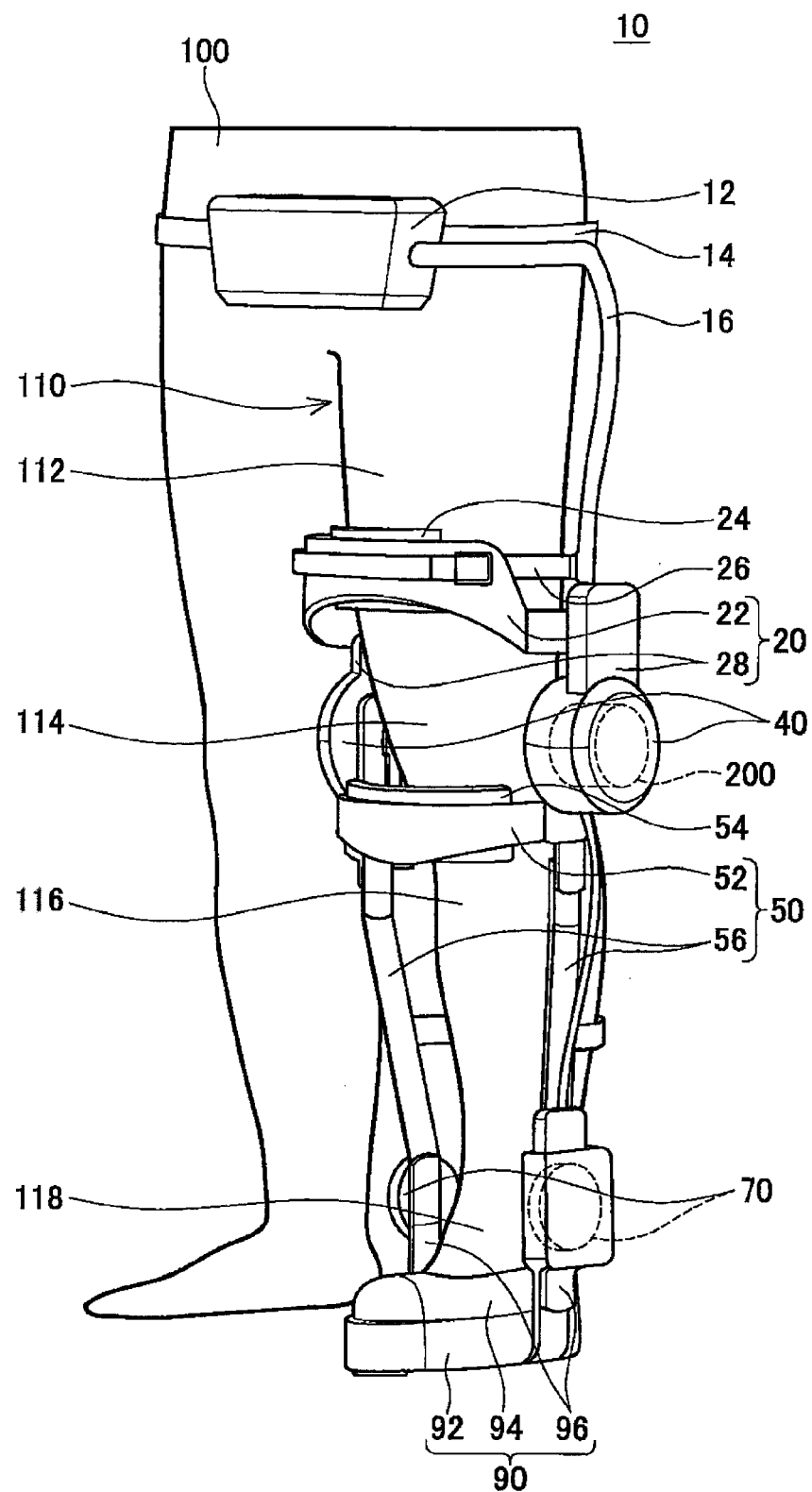
FIG. 1 shows a schematic front view of a walking assistance device 10.

An embodiment of the present invention will be described with reference to the figures. FIG. 1 shows a walking assistance device 10 of the embodiment. As shown in FIG. 1, the walking assistance device 10 is a device to assist walking of a user 100, and is a device that can be fitted onto the user 100. The walking assistance device 10 is used, e.g., for rehabilitation of the user 100 who has developed trouble in walking independently. By using the walking assistance device 10, the functional recovery of the user 100 can be facilitated, and the efforts of an attendant assisting the user 100 can also be reduced.

The walking assistance device 10 comprises a control unit 12, an upper leg frame 20, a lower leg frame 50, and a foot frame 90. The control unit 12 contains a small-scale computer device and battery and, in addition to supplying power to the parts of the walking assistance device 10, also controls the operation of the parts of the walking assistance device 10. The control unit 12 is attached, as an example, to the trunk (waist) of the user 100. The control unit 12 is provided on a mounting belt 14 to be fixed to the trunk of the user 100. Moreover, there is no particular restriction on the position where the control unit 12 is fitted, e.g., the control unit 12 may be configured to be fitted onto the back of the user 100.

The upper leg frame 20, the lower leg frame 50, and the foot frame 90 are fitted onto an affected leg 110, this being the leg (here, the left leg) of the user 100 requiring assistance. Specifically, the upper leg frame 20 is fitted to an upper leg 112, the lower leg frame 50 is fitted to a lower leg 116, and the foot frame 90 is fitted onto a foot 118.

The upper leg frame 20 has an upper leg support 22 and a pair of upper leg links 28. The upper leg support 22 connects the pair of upper leg links 28. The upper leg support 22 is disposed at the front of the upper leg 112 of the user 100. The upper leg links 28 are each disposed at the sides of the upper leg 112 of the user 100. A pad 24 and a belt 26 are provided on the upper leg support 22. The upper leg frame 20 can be fitted to the upper leg 112 by fastening the belt 26. The pad 24 makes contact with the front surface of the upper leg 112.

The lower leg frame 50 has a lower leg support 52 and a pair of lower leg links 56. The lower leg support 52 connects the pair of lower leg links 56. The lower leg support 52 is disposed at the front of the lower leg 116 of the user 100. The lower leg links 56 are each disposed at the sides of the lower leg 116 of the user 100. A pad 54 is provided on the lower leg support 52. The pad 54 makes contact with the front surface of the lower leg 116.

The upper leg frame 20 and the lower leg frame 50 are connected via a pair of knee joint mechanisms 40. Each of the knee joint mechanisms 40 is a uniaxial joint mechanism, and connects the upper leg links 28 of the upper leg frame 20 with the lower leg links 56 of the lower leg frame 50 in a manner allowing swinging. The knee joint mechanisms 40 positioned at the outer sides of the affected leg 110 house an actuator (e.g., a motor) for rotating the knee, a reduction gear, an angle sensor, a rotation restricting device 200, etc., and are driving units for swinging the upper leg frame 20 and the lower leg frame 50 relative to one another. The knee joint mechanisms 40 are connected to the control unit 12 via an electrical cord 16, are operated by electric power from the control unit 12, and their operation is controlled by the control unit 12. As an example, the control unit 12 stores target data describing a target angle of the knee joint mechanisms 40 over time, and controls the actuators of the knee joint mechanisms 40 such that the actual angle of the knee joint mechanisms 40 conforms to the target angle.

The foot frame 90 has a foot plate 92, a shoe 94, and a pair of foot links 96. The foot plate 92 connects the pair of foot links 96. The shoe 94 is formed on an upper surface of the foot plate 92 (the surface facing the foot 118). The shoe 94 has the same shape as a common shoe. When the shoe 94 is fitted onto the foot 118 of the user 100, the foot plate 92 is disposed below the foot 118 of the user 100 (at the sole of the foot). Further, the foot links 96 are disposed to the sides of the foot 118 of the user 100.

The lower leg frame 50 and the foot frame 90 are connected via a pair of ankle joint mechanisms 70. Each of the ankle joint mechanisms 70 is a uniaxial joint mechanism, and connects the lower leg links 56 of the lower leg frame 50 with the foot links 96 of the foot frame 90 in a manner allowing swinging.

According to the above configuration, the walking assistance device 10 is attached primarily to the affected leg 110 of the user 100, and can assist the walking of the user 100 by adjusting the movement of the affected leg 110. Moreover, there is no particular restriction on the operation mode of the walking assistance device 10, and the walking assistance device 10 may almost completely control the movement of the affected leg 110, or may apply assisting force following the movement of the affected leg 110.

Figure 2:
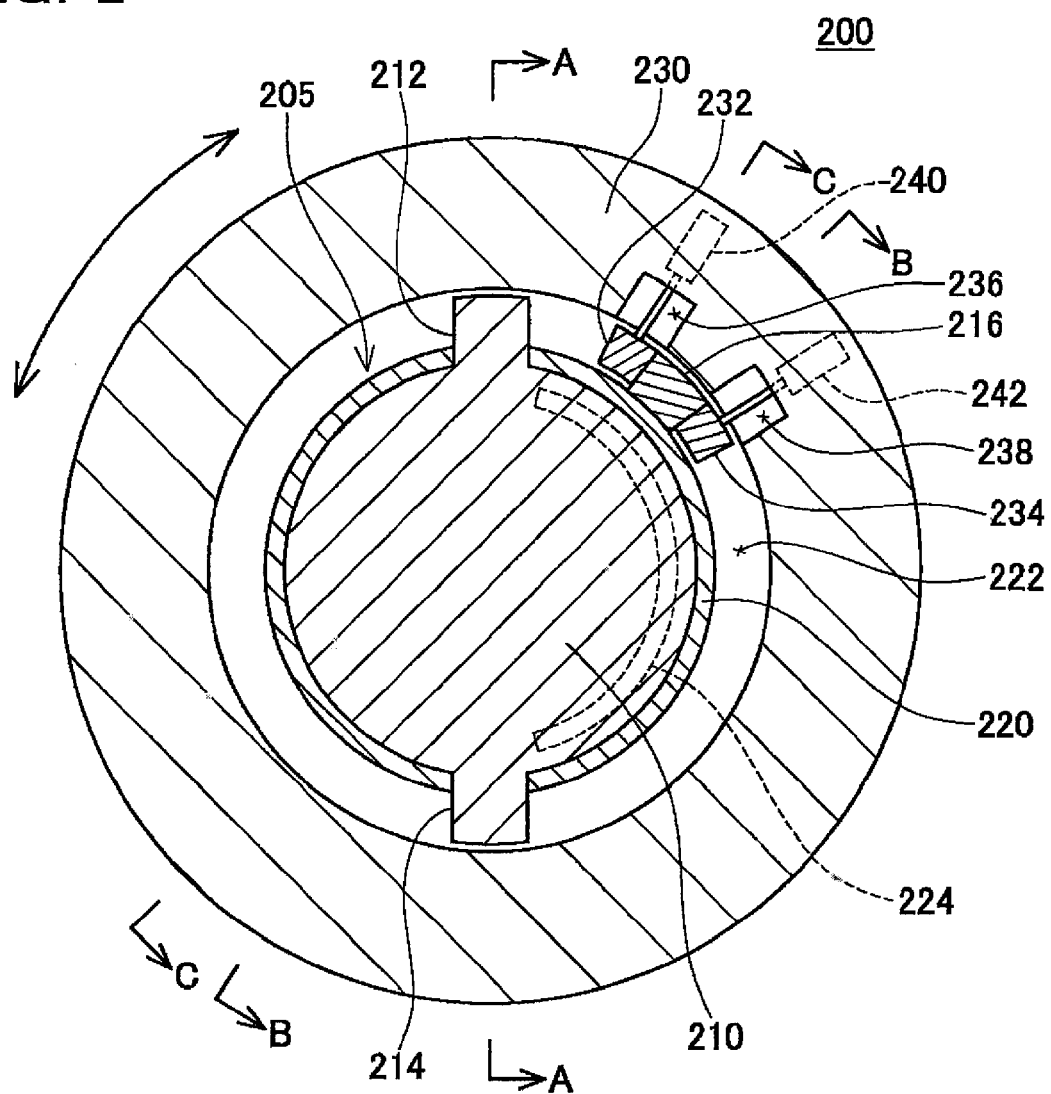
FIG. 2 shows a schematic top view of a rotation restricting device 200.

FIGS. 2 and 3 schematically show the configuration of the rotation restricting device 200 contained in the knee joint mechanism 40. The rotation restricting device 200 comprises a base part 205 and a rotating part 230. The base part 205 comprises a first base part 210 and a second base part 220 each formed in a disk shape. The first base part 210 and the second base part 220 are disposed coaxially, and are fixed to one another. The rotating part 230 is formed in a hollow cylindrical shape, and is disposed coaxially with the first base part 210 and the second base part 220 of the base part 205. The base part 205 is joined to an upper end of the lower leg link 56. The rotating part 230 is joined to a lower end of the upper leg link 28. When the actuator for rotating the knee is driven by the control unit 12, the rotating part 230 rotates relative to the base part 205 around the center of rotation of central axes of the first base part 210, the second base part 220 and the rotating part 230. A sliding space 222 is formed between the base part 205 and the rotating part 230.

Fixed stoppers 212, 214 are formed on the first base part 210. The fixed stoppers 212, 214 are disposed so as to protrude from the first base part 210 into the sliding space 222. In the example shown in FIG. 2, the fixed stoppers 212, 214 are set in positions mutually separated by 180°. Moreover, the relative positional relationship of the fixed stoppers 212, 214 is not restricted to this, but may be set as required.

A sliding stopper 216 and an electromagnetic lock 224 are provided on the second base part 220. The sliding stopper 216 is capable of sliding along an outer circumference of the second base part 220 within the sliding space 222. In other words, the sliding stopper 216 is capable of rotating around the central axis of the base part 205, and the sliding space 222 becomes a rotation path of the sliding stopper 216. The electromagnetic lock 224 locks and releases the sliding of the sliding stopper 216 with respect to the second base part 220. When the electromagnetic lock 224 is in an OFF state, the sliding stopper 216 can slide with respect to the second base part 220. When the electromagnetic lock 224 is in an ON state, the sliding stopper 216 is fixed with respect to the second base part 220. An example of the specific configuration of the electromagnetic lock 224 is as follows. Holes are formed in an outer circumference surface of the second base part 220 separated by a predetermined angle (e.g., 1°). Pins moved by a solenoid actuator are provided on the sliding stopper 216. The pins of the sliding stopper 216 are configured to be inserted into the holes of the second base part 220 by magnetic force when the electromagnetic lock 224 is turned ON. When the pins of the sliding stopper 216 are inserted into the holes of the second base part 220, the sliding stopper 216 is fixed with respect to the second base part 220.

Blocks 232, 234 are provided on the rotating part 230. Housing parts 236, 238 that house the blocks 232, 234 are formed on the rotating part 230. The blocks 232, 234 can be moved in a radial direction of the rotating part 230 by solenoid actuators 240, 242 contained in the rotating part 230. When the solenoid actuators 240, 242 are turned ON, the blocks 232, 234 are retracted from the sliding space 222 into the housing parts 236, 238. When the solenoid actuators 240, 242 are turned OFF, the blocks 232, 234 protrude toward the sliding space 222 from the housing parts 236, 238. The positions in which the blocks 232, 234 are attached are set such that a space when the two are pushed into the sliding space 222 is approximately identical to the width of the sliding stopper 216. Moreover, the block 232 may be called the first block 232, and the block 234 may be called the second block.

Figure 3A:
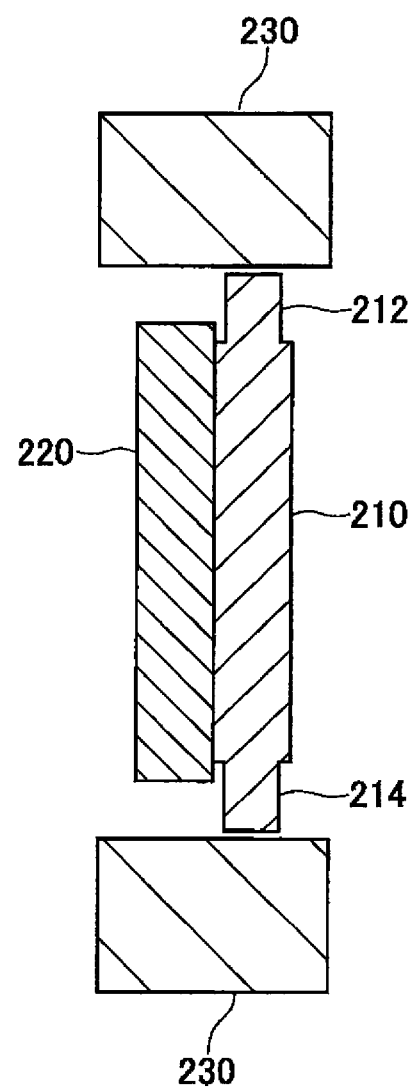
FIG. 3A shows a schematic longitudinal cross-sectional view of the rotation restricting device 200 along the cross-section A-A of FIG. 2.
Figure 3B:
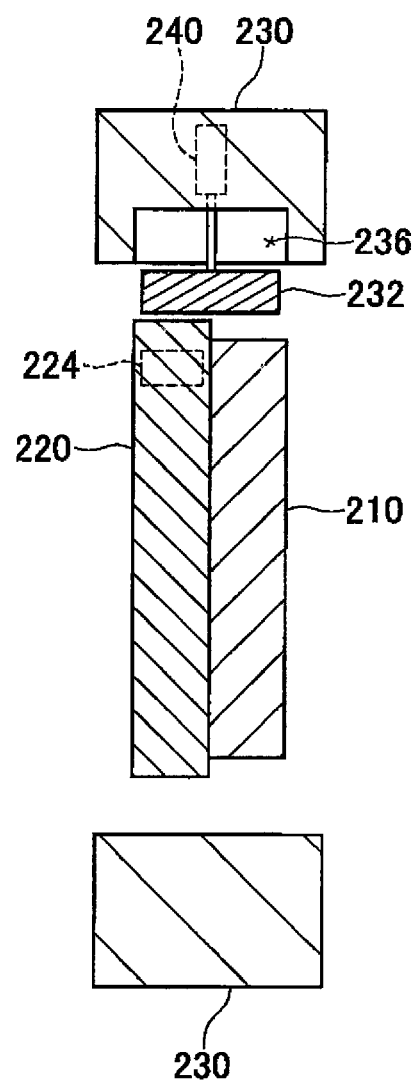
FIG. 3B shows a schematic longitudinal cross-sectional view of the rotation restricting device 200 along the cross-section B-B of FIG. 2.
Figure 3C:
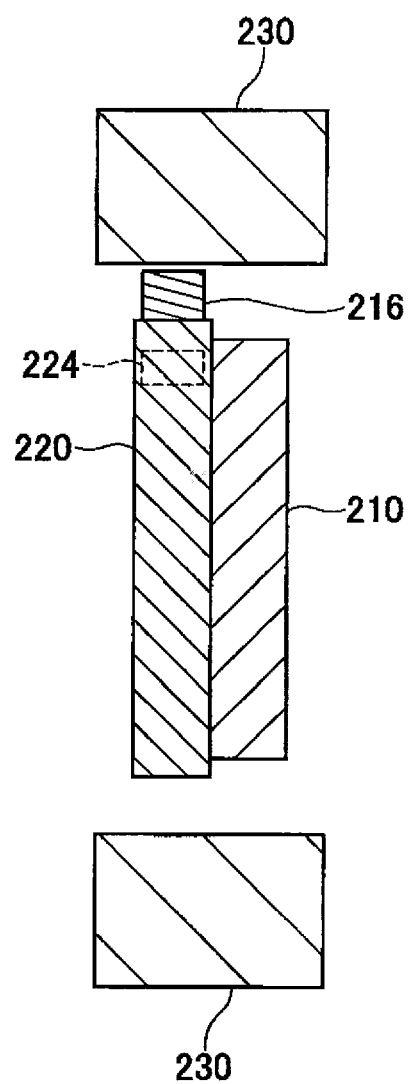
FIG. 3C shows a schematic longitudinal cross-sectional view of the rotation restricting device 200 along the cross-section C-C of FIG. 2.

As shown in FIG. 3A, the thickness of the fixed stoppers 212, 214 is approximately identical to that of the first base part 210, the fixed stoppers 212, 214 being formed to be slightly thinner than the first base part 210. As shown in FIG. 3C, the thickness of the sliding stopper 216 is approximately identical to that of the second base part 220, the sliding stopper 216 being formed to be slightly thinner than the second base part 220. As shown in FIG. 3B, the thickness of the block 232 is approximately identical to the total thickness of the first base part 210 and the second base part 220, the block 232 being formed to be slightly thinner than the total thickness of the first base part 210 and the second base part 220. Moreover, the block 232 is shown in FIG. 3B, but the same applies for the block 234. Consequently, in a state where the blocks 232, 234 protrude into the sliding space 222, the blocks 232, 234 have a positional relationship where they interfere with both the fixed stoppers 212, 214 and the sliding stopper 216. More precisely, the blocks 232, 234 interfere with a movement path of the sliding stopper 216.

The operation of the electromagnetic lock 224 and the solenoid actuators 240, 242 is controlled by the control unit 12.

The operation of the rotation restricting device 200 will be described below. In the case where the walking assistance device 10 is operated normally, both the electromagnetic lock 224 and the solenoid actuators 240, 242 of FIG. 2 are OFF. In this case, the sliding stopper 216 can slide freely along the outer circumference of the second base part 220, and both the blocks 232, 234 are protruding into the sliding space 222. When, in this state, the knee joint mechanisms 40 are rotated and the rotating part 230 is rotated relative to the base part 205, the sliding stopper 216 slides, in a state of being gripped by the blocks 232, 234, along the outer circumference of the second base part 220 following the rotation of the rotating part 230. In this case, the rotating part 230 can rotate anti-clockwise with respect to the base part 205 until the block 232 makes contact with the fixed stopper 212, and can rotate clockwise until the block 234 makes contact with the fixed stopper 214. I.e., during normal operation of the walking assistance device 10, the rotation range of the knee joint mechanisms 40 is regulated by the fixed stoppers 212, 214.

In the case where the walking assistance device 10 has malfunctioned, the rotation of the knee joint mechanisms 40 can be restricted using the rotation restricting device 200. The rotation restricting device 200 of the present embodiment restricts the rotation of the knee joint mechanisms 40 in any of the following modes described below: (1) total rotation prevention, (2) clockwise rotation prevention, (3) anti-clockwise rotation prevention. The mode for restricting the rotation of the knee joint mechanisms 40 can be selected as appropriate in the control unit 12.

(1) Total Rotation Prevention

In the case of totally preventing the rotation of the knee joint mechanisms 40, the control unit 12 turns ON the electromagnetic lock 224, and turns OFF the solenoid actuators 240, 242. In this case, the sliding stopper 216 is fixed with respect to the second base part 220 by the electromagnetic lock 224. Further, both the blocks 232, 234 are protruding into the sliding space 222. In this state, since the sliding stopper 216 is gripped by the blocks 232, 234, and further the sliding stopper 216 is fixed with respect to the second base part 220, the rotating part 230 is prevented from rotating with respect to the base part 205 in either the clockwise direction or anti-clockwise direction of FIG. 2. The rotation of the knee joint mechanisms 40 can be totally locked.

(2) Clockwise Rotation Prevention

Figure 4:
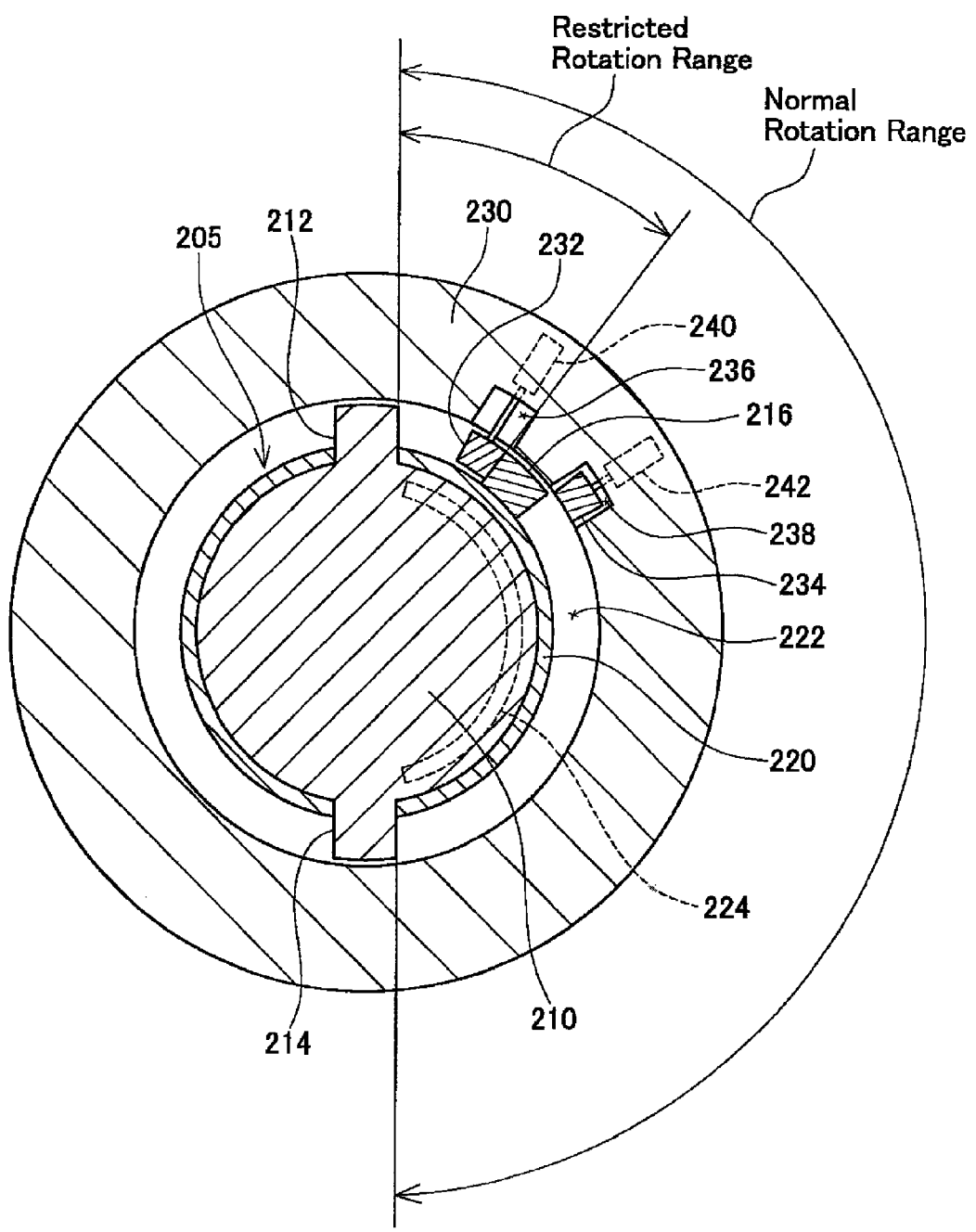
FIG. 4 is a figure schematically showing clockwise rotation being prevented by the rotation restricting device 200.

In the case of preventing rotation of the knee joint mechanisms 40 in the clockwise direction, the control unit 12 turns ON the electromagnetic lock 224, turns OFF the solenoid actuator 240, and turns ON the solenoid actuator 242. In this case, as shown in FIG. 4, the sliding stopper 216 is fixed with respect to the second base part 220, the block 234 is retracted into the housing part 238, and the block 232 remains protruding into the sliding space 222. In this state, the rotating part 230 can rotate with respect to the base part 205 in the clockwise direction of FIG. 4 until the block 232 makes contact with the sliding stopper 216, and can rotate in the anti-clockwise direction until the block 232 makes contact with the fixed stopper 212. I.e., the knee joint mechanisms 40 can rotate in the clockwise direction until reaching the rotation angle of the time the electromagnetic lock 224 was turned ON, and can rotate in the anti-clockwise direction for a range identical to that of normal operation. Consequently, the rotation of the knee joint mechanisms 40 can be restricted to a narrower range than the rotation range of the knee joint mechanisms 40 during normal operation of the walking assistance device 10.

(3) Anti-Clockwise Rotation Prevention

Figure 5:
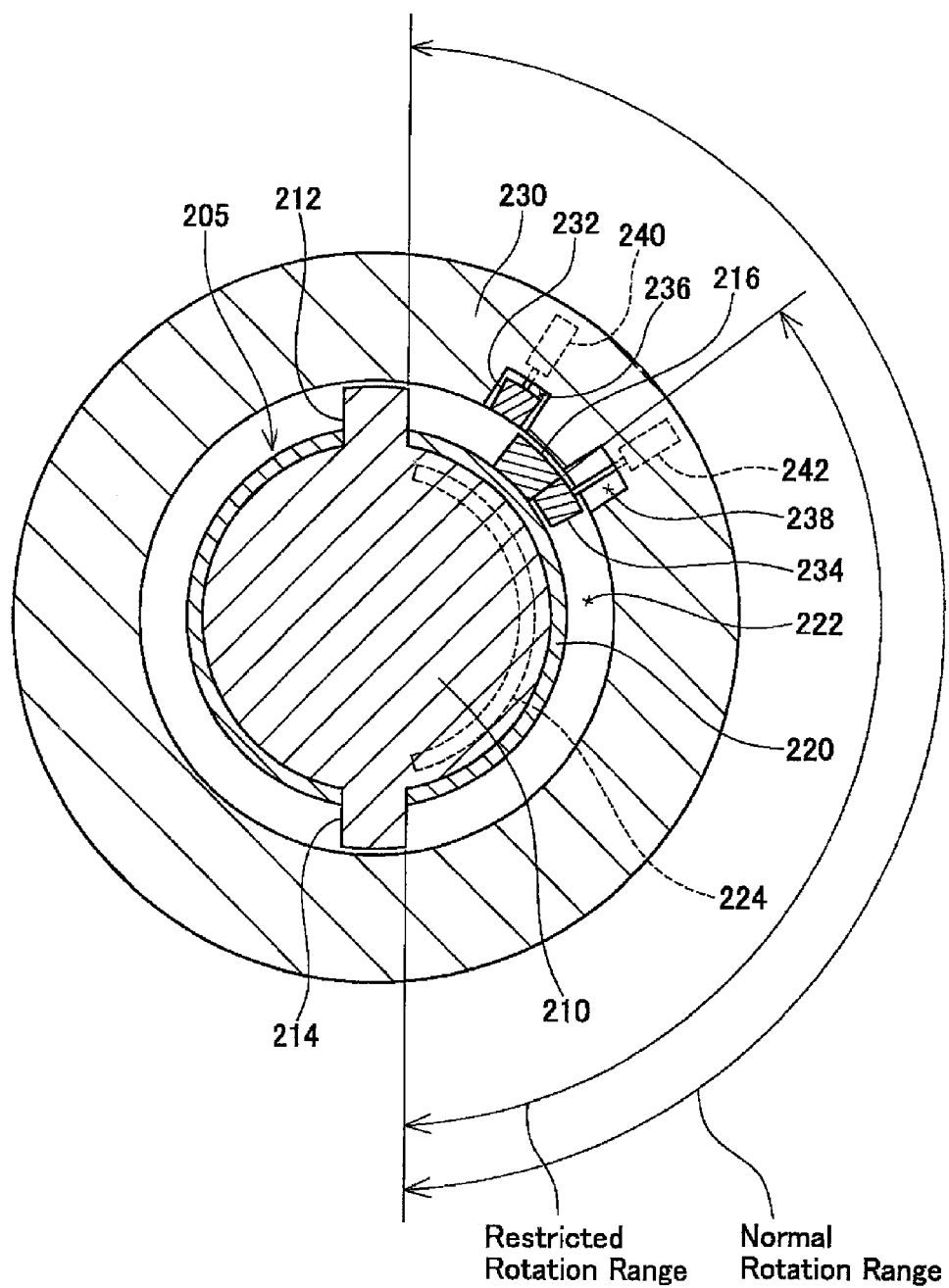
FIG. 5 is a figure schematically showing anti-clockwise rotation being prevented by the rotation restricting device 200.

In the case of preventing rotation of the knee joint mechanisms 40 in the anti-clockwise direction, the control unit 12 turns ON the electromagnetic lock 224, turns ON the solenoid actuator 240, and turns OFF the solenoid actuator 242. In this case, as shown in FIG. 5, the sliding stopper 216 is fixed with respect to the second base part 220, the block 232 is retracted into the housing part 236, and the block 234 remains protruding into the sliding space 222. In this state, the rotating part 230 can rotate with respect to the base part 205 in the clockwise direction of FIG. 5 until the block 234 makes contact with the fixed stopper 214, and can rotate in the anti-clockwise direction until the block 234 makes contact with the sliding stopper 216. I.e., the knee joint mechanisms 40 can rotate in the clockwise direction for a range identical to that of normal operation, and can rotate in the anti-clockwise direction until reaching the rotation angle of the time the electromagnetic lock 224 was turned ON. Consequently, the rotation of the knee joint mechanisms 40 can be restricted to a narrower range than the rotation range of the knee joint mechanisms 40 during normal operation of the walking assistance device 10.

According to the rotation restricting device 200 of the present embodiment, as above, the rotation range of the knee joint mechanisms 40 can be changed to a rotation range narrower than that during normal operation by using the electromagnetic lock 224 to lock the sliding stopper 216 which slides along the outer circumference of the second base part 220. Even in the case where one wants to temporarily restrict the rotation range of the knee joint mechanisms 40, as in the case where the walking assistance device 10 has malfunctioned, etc., the rotation of the knee joint mechanisms 40 can be restricted properly. Additionally, should the control unit 12 or the actuator for rotating the knee run wildly, the user's safety can be ensured by making the rotation range of the knee joint mechanisms 40 narrower using the rotation restricting device 200.

Further, according to the rotation restricting device 200 of the present embodiment, in the case where the walking assistance device 10 has malfunctioned while the user is walking, the rotation range of the knee joint mechanisms 40 can be restricted, without totally preventing the rotation of the knee joint mechanisms 40, by performing the aforementioned clockwise rotation prevention of (2) or the anti-clockwise rotation prevention of (3). If the rotation of the knee joint mechanisms 40 is prevented totally, the user must continue walking with his knee remaining in a bent or extended state, possibly leading to the user falling. Such a situation can be forestalled using the rotation restricting device 200 of the present embodiment.

In the case where the rotation of the knee joint mechanisms 40 is restricted by the rotation restricting device 200 of the present embodiment, the restricted rotation range is regulated by the position of the sliding stopper 216 at the time it is locked by the electromagnetic lock 224. Consequently, the rotation range to be restricted by the rotation restricting device 200 can be adjusted while the knee joint mechanisms 40 are actually being rotated. The rotation range of the knee joint mechanisms 40 can be adjusted conveniently without performing an operation such as part replacement, etc.

While the clockwise rotation prevention of (2) or the anti-clockwise rotation prevention of (3) is being performed, the sliding stopper 216 enters a separated state from the blocks 232, 234 when the rotating part 230 rotates relative to the base part 205. Consequently, in the case of releasing the rotation restriction performed by the rotation restricting device 200 and returning to normal operation of the walking assistance device 10, the sliding stopper 216 must be returned to the position of being gripped by the two blocks 232, 234. For this purpose, e.g., a configuration may be provided in which an actuator for sliding is disposed separately, this sliding the sliding stopper 216. By providing this type of actuator for sliding, the sliding stopper 216 can be returned to the position where it is gripped by the two blocks 232, 234 while the walking assistance device 10 remains fitted onto the user. In this case, a configuration may be provided in which a one-way clutch is further provided on the sliding stopper 216, this preventing sliding in the opposite direction while the actuator for sliding is returning the sliding stopper 216 to the position where it is gripped by the two blocks 232, 234. By providing this type of configuration, even in the case of malfunctioning while the sliding stopper 216 is being returned, the situation can be prevented where the sliding stopper 216 slides in the opposite direction.

Figure 6:
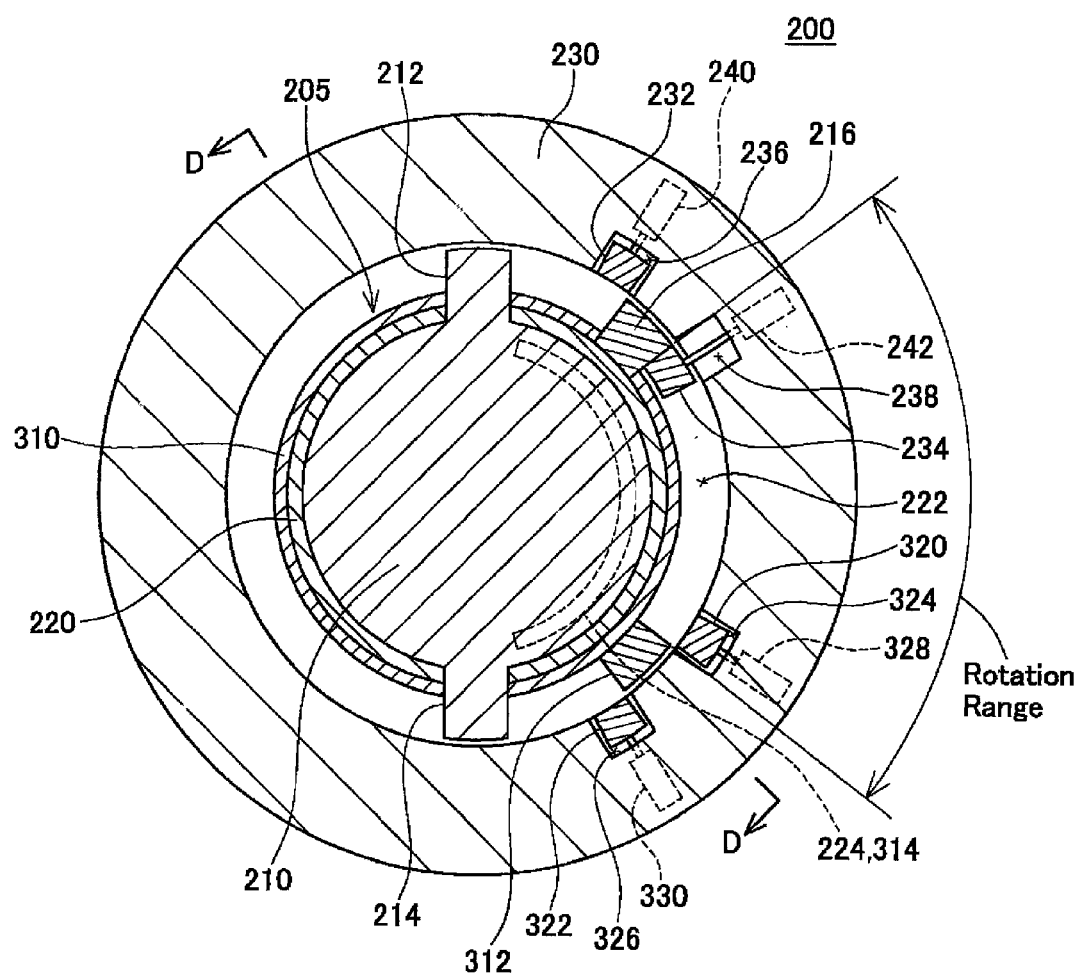
FIG. 6 shows a schematic top view of a variant of the rotation restricting device 200.
Figure 7:
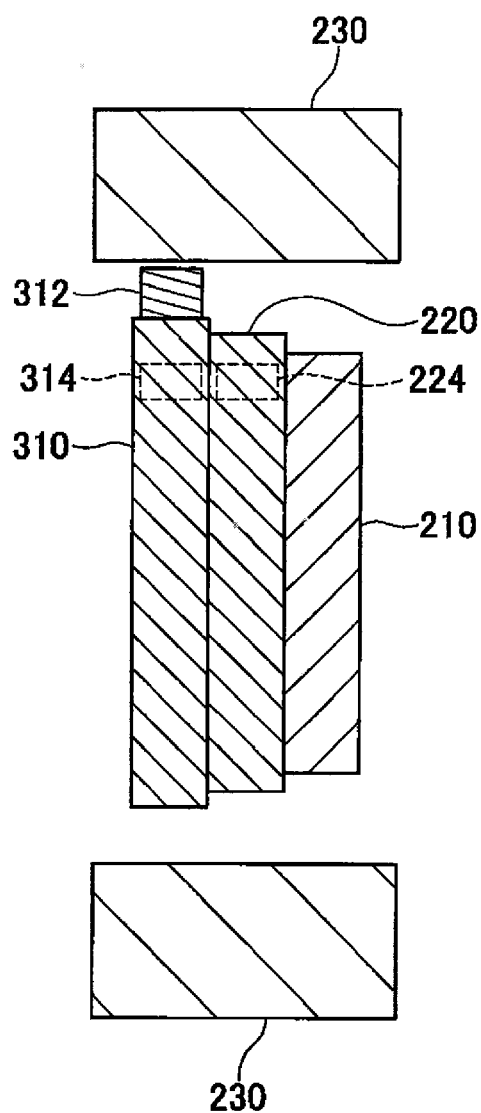
FIG. 7 shows a schematic longitudinal cross-sectional view of the variant of the rotation restricting device 200 along the cross-section D-D of FIG. 6.

Moreover, a form was described in the above embodiment wherein the sliding stopper 216 and the electromagnetic lock 224 are provided as one set. However, a configuration provided with a plurality of sets of sliding stoppers and electromagnetic locks is possible. FIGS. 6 and 7 show the configuration of the rotation restricting device 200 in the case of two sets of sliding stoppers and electromagnetic locks being provided. In the example shown in FIGS. 6 and 7, the base part 205 comprises the first base part 210, the second base part 220, and a third base part 310. The third base part 310 is formed in a disk shape, and is fixed coaxially to the first base part 210 and the second base part 220. A sliding stopper 312 and an electromagnetic lock 314 are provided on the third base part 310. The sliding stopper 312 can slide along the outer circumference of the third base part 310 within the sliding space 222. The electromagnetic lock 314 locks and releases the sliding of the sliding stopper 312 with respect to the third base part 310.

Blocks 320, 322 are provided on the rotating part 230. Housing parts 324, 326 that house the blocks 320, 322 are formed on the rotating part 230. The blocks 320, 322 can be moved in a radial direction of the rotating part 230 by solenoid actuators 328, 330 contained in the rotating part 230. When the solenoid actuators 328, 330 are turned ON, the blocks 320, 322 are retracted from the sliding space 222 into the housing parts 324, 326. When the solenoid actuators 328, 330 are turned OFF, the blocks 320, 322 protrude toward the sliding space 222 from the housing parts 324, 326. The positions in which the blocks 320, 322 are attached are set such that the space when the two are pushed into the sliding space 222 is approximately identical to the width of the sliding stopper 216.

In the aforementioned configuration, when the electromagnetic locks 224, 314 are turned ON, the solenoid actuator 242 is turned OFF, and the solenoid actuators 240, 328, 330 are turned ON, as shown in FIG. 6, the sliding stopper 216 is fixed with respect to the second base part 220, the sliding stopper 312 is fixed with respect to the third base part 310, the blocks 232, 320, 322 are retracted into the housing parts 236, 324, 326, and the block 234 remains protruding into the sliding space 222. In this state, the rotating part 230 can rotate with respect to the base part 205 in the clockwise direction of FIG. 6 until the block 234 makes contact with the sliding stopper 312, and can rotate in the anti-clockwise direction until the block 234 makes contact with the sliding stopper 216. i.e., in both the clockwise and anti-clockwise directions, the rotation of the knee joint mechanisms 40 can be restricted to a narrower range than the rotation range of the knee joint mechanisms 40 during normal operation of the walking assistance device 10.

Points to be noted of the embodiment will be described. The rotation restricting device 200 of the embodiment is a device restricting the rotation of the rotating part 230 with respect to the base part 205. The rotation restricting device 200 comprises a moveable stopper (the sliding stoppers 216, 312), a lock mechanism (the electromagnetic lock 224), and a first retractable block (the block 232). The moveable stopper is supported by the base part 205, and can move along a peripheral direction of the base part. The lock mechanism can prevent movement of the moveable stopper. Moreover, when the lock mechanism is released, the moveable stopper can move freely along the peripheral direction. The first retractable block is provided on the rotating part, and is configured such that it can be retracted from a first position interfering with a movement path of the moveable stopper to a second position not interfering with the movement path. The moveable stopper and the first retractable block restrict the rotation range of the rotating part by engaging the lock mechanism to prevent the movement of the moveable stopper and by positioning the first retractable block in the first position.

The rotation restricting device 200 of the embodiment further comprises a second retractable block (the block 234) that is provided on the rotating part and that can be retracted from a third position interfering with the movement path of the moveable stopper to a fourth position not interfering with the movement path. A space between the first retractable block positioned in the first position and the second retractable block positioned in the third position is essentially equal to the length of the moveable stopper in its peripheral direction.

Specific examples of the present invention are described above in detail, but these examples are merely illustrative and place no limitation on the scope of the patent claims. The technology described in the patent claims also encompasses various changes and modifications to the specific examples described above. The technical elements explained in the present specification or drawings provide technical utility either independently or through various combinations, and are not limited to the combinations described at the time the claims are filed. Further, the purpose of the examples illustrated by the present specification or drawings is to satisfy multiple objectives simultaneously, and satisfying any one of those objectives gives technical utility to the present invention.

REFERENCE SIGNS LIST

10 Walking assistance device, 12 Control unit, 14 Mounting belt, 16 Electrical cord, 20 Upper leg frame, 22 Upper leg support, 24 Pad, 26 Belt, 28 Upper leg link, 40 Knee joint mechanism, 50 Lower leg frame, 52 Lower leg support, 54 Pad, 56 Lower leg link, 70 Ankle joint mechanism, 90 Foot frame, 92 Foot plate, 94 Shoe, 96 Foot link, 100 User, 110 Affected leg, 112 Upper leg, 116 Lower leg, 118 Foot, 200 Rotation restricting device, 205 Base part, 210 First base part, 212, 214 Fixed stopper, 216, 312 Sliding stopper, 220 Second base part, 222 Sliding space, 224, 314 Electromagnetic lock, 230 Rotating part, 232, 234, 320, 322 Block, 236, 238, 324, 326 Housing part, 240, 242, 328, 330 Solenoid actuator, 310 Third base part.

The invention claimed is:

1. A rotation restricting device for restricting the rotation of a rotating part with respect to a base part, comprising:
   a stopper supported so as to be capable of rotating around an axis of rotation of the base part,
   a lock mechanism capable of switching between a state preventing and a state allowing the rotation of the stopper with respect to the base part,
   a first block provided on the rotating part and capable of moving between a position interfering with and a position not interfering with a rotation path of the stopper, and
   a second block provided on the rotating part and capable of moving between a position interfering with and a position not interfering with the rotation path of the stopper, wherein
   in a state where the rotation of the rotating part with respect to the base part is not restricted, both the first block and the second block are in the position interfering with the rotation path of the stopper, and the stopper is positioned between the first block and the second block.

2. The rotation restricting device according to claim 1, wherein
   a space between the first block in the position interfering with the rotation path of the stopper and the second block in the position interfering with the rotation path of the stopper is equal to a width of the stopper along its rotation direction.

3. A robot joint comprising a rotation restricting device for restricting rotation of a rotating part with respect to a base part, the rotation restricting device comprising:
   a stopper supported so as to be capable of rotating around an axis of rotation of the base part,
   a lock mechanism capable of switching between a state preventing and a state allowing the rotation of the stopper with respect to the base part,
   a first block provided on the rotating part and capable of moving between a position interfering with and a position not interfering with a rotation path of the stopper, and
   a second block provided on the rotating part and capable of moving between a position interfering with and a position not interfering with the rotation path of the stopper, wherein
   in a state where the rotation of the rotating part with respect to the base part is not restricted, both the first block and the second block are in the position interfering with the rotation path of the stopper, and the stopper is positioned between the first block and the second block.

4. A robot joint for a walking assistance device comprising:
a rotation restricting device for restricting rotation of a rotating part with respect to a base part, the rotation restricting device comprising:
a stopper supported so as to be capable of rotating around an axis of rotation of the base part,
a lock mechanism capable of switching between a state preventing and a state allowing the rotation of the stopper with respect to the base part,
a first block provided on the rotating part and capable of moving between a position interfering with and a position not interfering with a rotation path of the stopper, and
a second block provided on the rotating part and capable of moving between a position interfering with and a position not interfering with the rotation path of the stopper, wherein
in a state where the rotation of the rotating part with respect to the base part is not restricted, both the first block and the second block are in the position interfering with the rotation path of the stopper, and the stopper is positioned between the first block and the second block.

* * * * *